United States Patent
Talbot et al.

[19]

[11] Patent Number: 6,106,751
[45] Date of Patent: Aug. 22, 2000

[54] METHOD FOR FABRICATING NEEDLES VIA CONFORMAL DEPOSITION IN TWO-PIECE MOLDS

[75] Inventors: Neil H. Talbot, San Francisco; Christopher G. Keller, El Cerrito; Albert P. Pisano, Livermore, all of Calif.

[73] Assignee: The Regents of the University of California, Oakland, Calif.

[21] Appl. No.: 09/044,398

[22] Filed: Mar. 18, 1998

[51] Int. Cl.7 .................................................. B22D 23/00
[52] U.S. Cl. ............................................................ 264/81
[58] Field of Search ................................................. 264/81

[56] References Cited

U.S. PATENT DOCUMENTS 5,383,512  1/1995  Jarvis ........................................ 164/46

OTHER PUBLICATIONS

Chen et al., "A Multichannel Neural Probe for Selective Chemical Delivery at the Cellular Level", Solid State Sensor and Actuator Workshop Hilton Head, SC Jun. 13–16, 1994.

Keller et al., "Milli–Scale Polysilicon Structures", Solid–State Sensor and Actuator Workshop Hilton Head, SC Jun. 13–16, 1994 note that p. 133 not reviewed, not present.

Keller et al., "Nickel–Filled Hexsil Thermally Actuated Tweezers", *Technical Digest*, Transducers 95, Stockholm, Sweden, Jun. 25–29, 1995, pp. 376–379.

*Primary Examiner*—Christopher A. Fiorilla
*Attorney, Agent, or Firm*—William S. Galliani; Pennie & Edmonds LLP

[57] ABSTRACT

A method of fabricating a needle via conformal deposition in a two-piece mold includes the step of attaching a top mold member to a bottom mold member such that the top mold member and the bottom mold member define an enclosed, elongated needle trench with a deposition aperture. A conformal substance, such as polysilicon, is then passed through the deposition aperture such that the conformal substance is deposited within the enclosed, elongated needle trench to form a needle. The method is used to form needles with prongs, multiple channels, multiple ports, barbs, strength enhancement features, and circuitry.

6 Claims, 8 Drawing Sheets

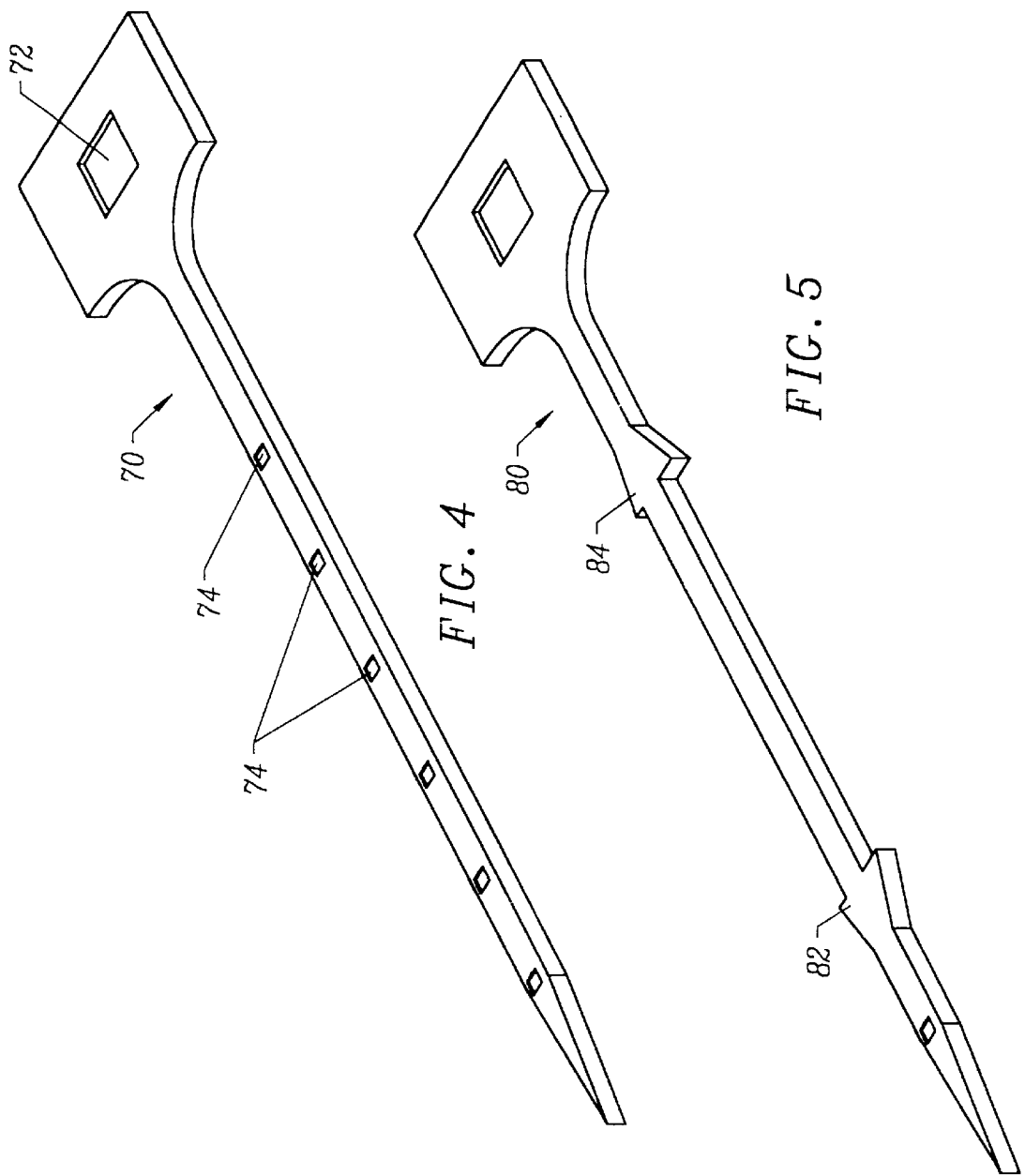

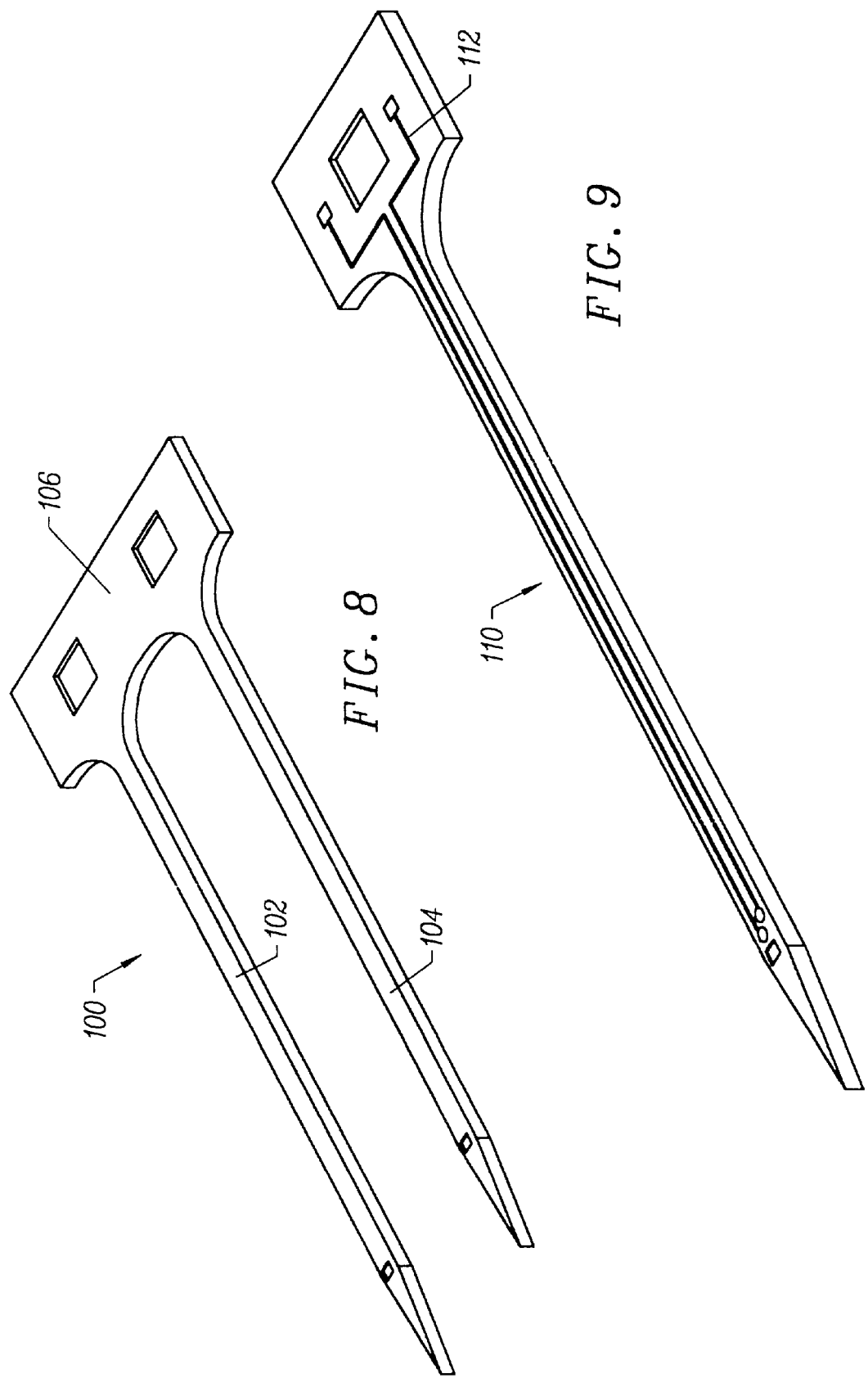

METHOD FOR FABRICATING NEEDLES VIA CONFORMAL DEPOSITION IN TWO-PIECE MOLDS

BRIEF DESCRIPTION OF THE INVENTION

This invention relates generally to hypodermic needles. More particularly, this invention relates to a technique for fabricating needles via conformal deposition in two-piece molds.

BACKGROUND OF THE INVENTION

Traditional machining techniques, such as, tube drawing, grinding, and polishing are used to fabricate needles. While satisfactory for simple needle designs, these techniques cannot be used to fabricate more sophisticated features and geometries that provide extended functionality. For example, a needle with two fluid channels to allow the simultaneous injection of two fluids to the same area is very difficult to fabricate with traditional needle machining techniques. Electronic circuitry, such as, electrodes and amplification circuitry may be used for charge delivery, electric field sensing, or electrophoretic pumping. Biological sensors to provide, for example, biological assay capability, would be extremely useful. Insertion and extraction limiting barbs are also potentially very useful. Additionally, a pump built into the needle and multiple inlet and outlet ports are highly desirable features. A dual prong needle would allow delivery through one prong and sensing in the other. These features are very difficult to implement with traditional machining.

Recently, silicon microfabrication techniques have been used to construct hypodermic needles. For example, microfabrication processes to produce needles are described in the work by Chen and Wise (J. Chen et al., "A Multichannel Neural Probe for the Selective Chemical Delivery at the Cellular Level", Solid State Sensor and Actuator Workshop, Hilton Head, S.C., 1994) and also by Linn (Liwei L. Linn, et al., "Silicon Processed Microneedles", *Technical Digest*, 7th International Conference on Solid-State Sensors and Actuators, Transducers '93, Yokohama, Japan, Jun. 7–10, 1993). There are two drawbacks with this early work. First, the disclosed processes are destructive to the wafer from which the needles are produced. Second, the processes do not rely upon a mold. Thus, new wafers must be used each time the process is repeated. This results in considerable added expense.

Single mold processes to make needles are known in the art. For example, the HexSi process invented by Chris Keller (Christopher G. Keller et al., "Nickel-Filled HexSi Thermally Actuated Tweezers", *Technical Digest*, Transducers 95, Stockholm, Sweden, Jun. 25–29, 1995, pp. 376–379) is a single wafer micromolding process. Unfortunately, the Hexsil process can only form relatively short needles (generally less than a millimeter).

In view of the foregoing, it would be highly desirable to provide an improved technique for fabricating hypodermic needles. Ideally, the technique would allow the fabrication of needles with extended functionality, such as multiple fluid channels, multiple ports, and integrated circuitry. In addition, the technique would preferably avoid prior art problems of limited needle length. Ideally, the technique would provide a re-usable mold process to reduce fabrication expense.

SUMMARY OF THE INVENTION

A method of fabricating a needle via conformal deposition in a two-piece mold includes the step of attaching a top mold member to a bottom mold member such that the top mold member and the bottom mold member define an enclosed, elongated needle trench with a deposition aperture. A conformal substance, such as polysilicon, is then passed through the deposition aperture such that the conformal substance is deposited within the enclosed, elongated needle trench to form a needle. The method is used to form needles with prongs, multiple channels, multiple ports, barbs, strength enhancement features, and circuitry.

The invention constitutes an improved technique for fabricating hypodermic needles. The re-usable mold process reduces fabrication expense. In addition, the mold process of the invention provides for longer needles than available in prior art mold processes.

BRIEF DESCRIPTION OF THE DRAWINGS

For a better understanding of the invention, reference should be made to the following detailed description taken in conjunction with the accompanying drawings, in which:

FIG. 4 is a perspective view of a needle with multiple fluid ports in accordance with an embodiment of the invention.

FIG. 5 is a perspective view of a needle with insertion and extraction barbs in accordance with an embodiment of the invention.

FIG. 8 is a perspective view of a dual prong needle in accordance with an embodiment of the invention.

FIG. 9 is a perspective view of a needle with circuitry in accordance with an embodiment of the invention.

Like reference numerals refer to corresponding parts throughout the drawings.

DETAILED DESCRIPTION OF THE INVENTION

Figure 1A:
FIG. 1a–1e illustrate the processing of a top mold member in accordance with an embodiment of the invention.

In brief, the invention includes a method of fabricating a needle via conformal deposition in a two-piece mold. The method includes the step of attaching a top mold member to a bottom mold member such that the top mold member and the bottom mold member define an enclosed, elongated needle trench with a deposition aperture. A conformal substance, such as polysilicon, is then passed through the deposition aperture such that the conformal substance is deposited within the enclosed, elongated needle trench to form a needle. The method is used to form needles with prongs, multiple channels, multiple ports, barbs, strength enhancement features, and circuitry, as demonstrated below.

The following processing steps have been used to construct a variety of devices, in accordance with the invention. Those skilled in the art will appreciate that a variety of modifications to the specified steps are feasible, yet still within the scope of the invention.

TABLE I

PREFERRED FABRICATION STEPS

A. STANDARD WAFER CLEAN
   VLSI lab sink
   Piranha clean ($H_2SO_4$:$H_2O_2$, 5:1) 10 minutes
   Two, one minute rinses in de-ionized (DI) water
   Rinse until resistivity of water is > 11 MΩ-cm
   Spin dry
   Piranha clean ($H_2SO_4$:$H_2O_2$, 5:1) 10 minutes
   Rinse in DI water for one minute
   Dip in 25: 1 HF until hydrophobic
   Two, one minute rinses in de-ionized (DI) water
   Rinse until resistivity of water is > 14 MΩ-cm
   Spin dry
B. CLEAN WAFERS WITH MINIMAL OXIDE STRIP
   VLSI lab sink
   Piranha clean ($H_2SO_4$:$H_2O_2$, 5:1) 10 minutes
   Rinse in DI water for one minute
   Dip in 25:1 HF briefly until native silicon oxide removed
   Two, one minute rinses in DI water
   Rinse until resistivity of DI water is > 14 MΩ-cm
   Spin dry
C. PARTIAL CLEAN WAFERS
   VLSI lab sink
   Piranha clean ($H_2SO_4$:$H_2O_2$, 5:1) 10 minutes
   Two, one minute rinses in de-ionized (DI) water
   Rinse until resistivity of water is > 11 MΩ-cm
   Spin dry
D. DEPOSIT LOW-STRESS SILICON NITRIDE
   Horizontal low pressure chemical vapor deposition reactor
   Target thickness as specified
   Conditions = 835° C., 140 mTorr, 100 sccm DCS, and 25 sccm $NH_3$
E. DEPOSIT PHOSPHOSILICATE GLASS (PSG)
   Horizontal low pressure chemical vapor deposition reactor
   Target thickness as specified
   Conditions = 450° C., 300 mTorr, 60 sccm $SiH_4$, 90 sccm $O_2$, and 10.3 sccm $PH_3$
   Step G. -- REFLOW PHOSPHOSILICATE GLASS
F. DEPOSIT LOW TEMPERATURE OXIDE (LTO)
   Horizontal low pressure chemical vapor deposition reactor
   Target thickness as specified
   Conditions = 450° C., 300 mTorr, 60 sccm $SiH_4$, 90 sccm $O_2$, and 10.3 sccm $PH_3$
   Step G. -- REFLOW PHOSPHOSILICATE GLASS
G. REFLOW PHOSPHOSILICATE GLASS
   Horizontal atmospheric pressure reactor
   Conditions = 1000° C., $N_2$, 1 hour
H. PHOTOLITHOGRAPHY
   1. HMDS prime
   2. Photoresist coat
      Coat 1 μm of Shipley S3813 (thickness may need to be varied depending on topography and thickness of material to be etched) multi-wavelength positive resist
   3. Expose resist
      G-Line wafer stepper
      Standard exposure time
   4. Resist develop
      Standard develop using Shipley MF 319
   5. Hard bake for 30 minutes
I. COAT BACKSIDE WITH PHOTORESIST
   1. HMDS prime
   2. Photoresist coat
      Coat 1 μm of Shipley S3813 (thickness may need to be varied depending on topography and thickness of material to etched) multi-wavelength positive resist
   3. Resist develop
      Standard develop using Shipley MF 319
   4. Hard bake for 30 minutes
J. OXIDE WET ETCHING
   VLSI lab sink
   Etch in 5:1 BHF until desired amount of oxide has been removed
   Two, one minute rinses in DI water
   Rinse until resistivity of water is > 11 MΩ-cm
   Spin dry
K. PHOTORESIST STRIP
   Lab sink
   PRS-2000, heated to 90° C., 10 minutes

TABLE I-continued

PREFERRED FABRICATION STEPS

Figure 1B:
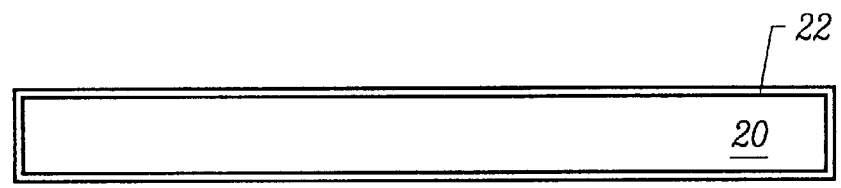
Figure 1C:
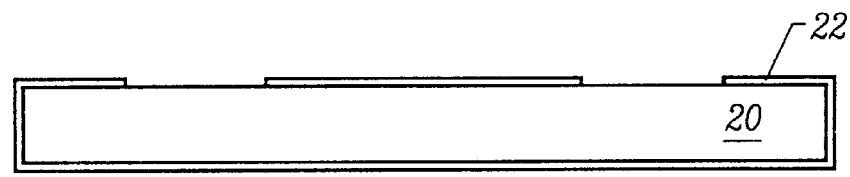
Figure 1D:
Figure 1E:
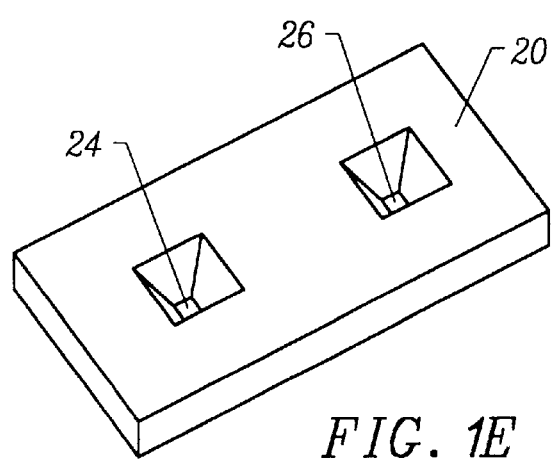

Rinse in three baths of DI water, 2 minutes each
   Step C. -- PARTIAL CLEAN WAFERS
L. SILICON NITRIDE ETCH
   $SF_6$ + He plasma etch
   Etch until desired amount of nitride has been removed
M. DEPOSIT UNDOPED POLYSILICON
   Horizontal low pressure chemical vapor deposition reactor
   Target thickness as specified
   Conditions = 580° C., 300 mTorr, and 100 sccm $SiH_4$
N. ANISOTROPIC POLYSILICON ETCH
   Chlorine plasma etch
   Etch until desired amount of polysilicon has been removed
O. NITROGEN ANNEAL
   Horizontal atmospheric pressure reactor
   Conditions = 1000° C., $N_2$, 1 hour
P. ANISOTROPHIC SILICON WET ETCH
   Lab sink, heated bath
   750 g KOH: 1500 ml $H_2O$
   Temperature: 80° C.
Q. OXIDE REMOVAL WET ETCHING
   Lab sink
   Etch in diluted HF or buffered HF until desired oxide removed
   Rinse in deionized water for approximately one hour
R. NEAR VERTICAL WALLED TRENCH ETCH
   Inductively coupled plasma etcher
   Advanced silicon etch process
   High plasma density low pressure processing system
   Fluorine plasma
   Etch to desired depth
S. SACRIFICIAL PSG AND SILICON NITRIDE REMOVAL
   Lab sink
   Concentrated HF dip with surfactant if needed, continue until desired sacrificial material has been removed
   Rinse for 2 minutes in two tanks of DI water
   Rinse for 120 minutes in third tank of DI water
T. SPUTTER GOLD
   Low pressure chamber
   Gold target
U. GOLD ETCH
   Lab sink
   Aqua regent etchant or other commercially available gold etchant
V. WET OXIDATION
   Horizontal atmospheric pressure reactor
   Conditions = Temperature as specified, water vapor environment
W. BORON DIFFUSION
   Horizontal atmospheric pressure reactor
   Solid source boron diffusion
   Conditions = Temperature as specified
X. DEPOSIT IN SITU DOPED POLYSIUCON
   Horizontal low pressure chemical vapor deposition reactor
   Target thickness as specified
   Conditions = 610° C. and 300 mTorr FIGS. 1a–1e illustrate the construction of a top mold member in accordance with an embodiment of the present invention. FIG. 1a illustrates a starting wafer 20, which may be 500 to 500 micron thick, <100> oriented, lightly doped silicon. The wafer is cleaned (Step A) and 4000 Å of silicon nitride is deposited (Step D). The resultant silicon nitride layer 22 is illustrated in FIG. 1b. Photolithography (Step H) is then performed. The silicon nitride is then etched (Step L). Preferably, 5000 Å is etched for a 25% over-etch. The photoresist is then stripped (Step K), to produce the device of FIG. 1c. An anisotropic silicon wet etch (Step P) is then performed through the wafer. Finally, the silicon nitride is removed (Step S). FIG. 1d provides a side view of the resultant device 20, while FIG. 1e provides a perspective view of the device 20. The top mold member 20 includes deposition apertures 24 and 26.

While FIGS. 1a–1e illustrate a single mold member 20, those skilled in the art will appreciate that typically over a thousand molds are prepared at once. Furthermore, the foregoing steps are only performed once to create the top mold member 20. Thereafter, the top mold member 20 can be reused to construct several batches of needles.

Figure 2A:
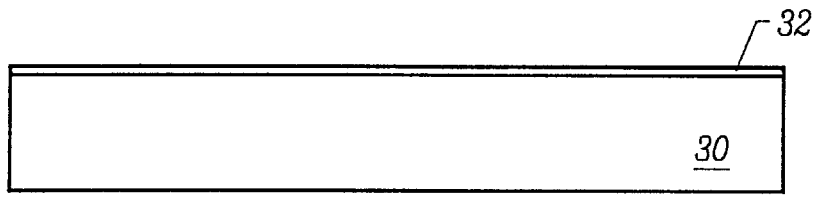
FIGS. 2a–2e illustrate the processing of a bottom mold member in accordance with an embodiment of the invention.
Figure 2B:
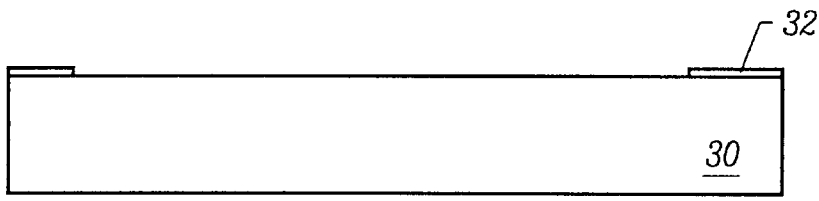
Figure 2C:
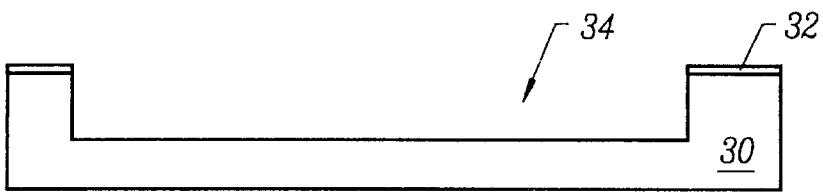
Figure 2D:
Figure 2E:
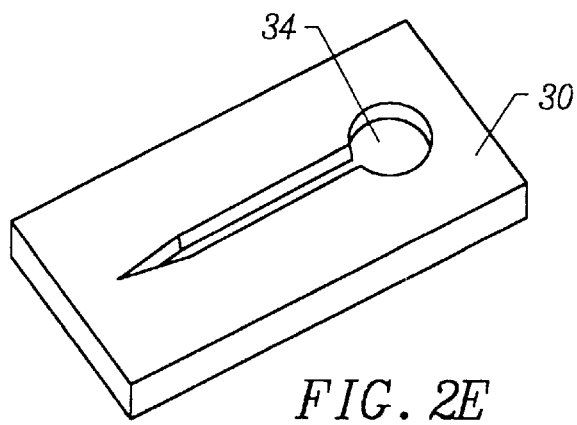

FIGS. 2a–2e illustrate the construction of a bottom mold member in accordance with an embodiment of the invention. FIG. 2a illustrates a starting wafer 30, which may be 500 to 500 micron thick, <100> oriented, lightly doped silicon. The wafer is cleaned (Step A). Thereafter, photoresist is spun onto the wafer 30, resulting in photoresist layer 32. Photolithography (Step H) is then performed to define a needle shape, which results in the device of FIG. 2b. A deep trench etch (Step R) is then performed to a depth of approximately 100 microns. The resultant needle trench 34 is illustrated in FIG. 2c. The photoresist is then stripped (Step K), to produce the device of FIG. 2d. FIG. 2d provides a side view of the resultant device 30, while FIG. 2e provides a perspective view of the device 30. The bottom mold member 30 includes a needle trench 34 defining the shape of a needle. In particular, the mold member 30 defines an elongated needle trench 34. When the top mold member 20 and the bottom mold member 30 are attached, an enclosed, elongated needle trench results. Deposition of a conformal substance into the trench produces a needle, as described below.

While FIGS. 2a–2e illustrate a single mold member, those skilled in the art will appreciate that typically over a thousand molds are prepared at once. Furthermore, the foregoing steps are only performed once to create the bottom mold member 30. Thereafter, the bottom mold member 30 can be reused to construct several batches of needles.

Figure 3A:
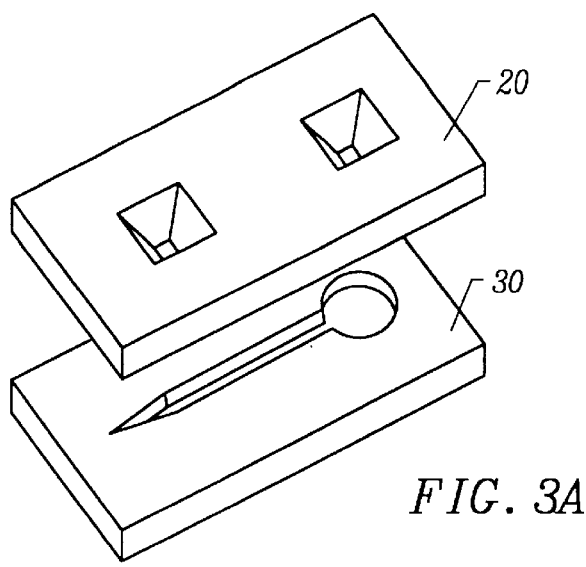
FIGS. 3a–3l illustrate the processing of a combined top mold member and bottom mold member in accordance with an embodiment of the invention.
Figure 3B:
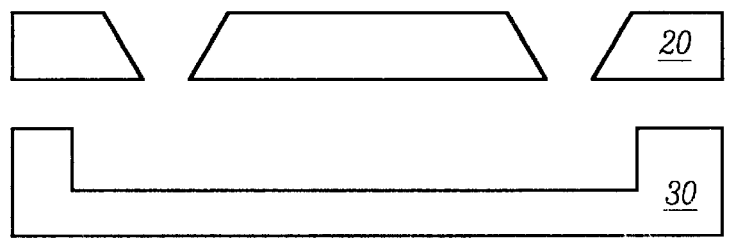
Figure 3C:
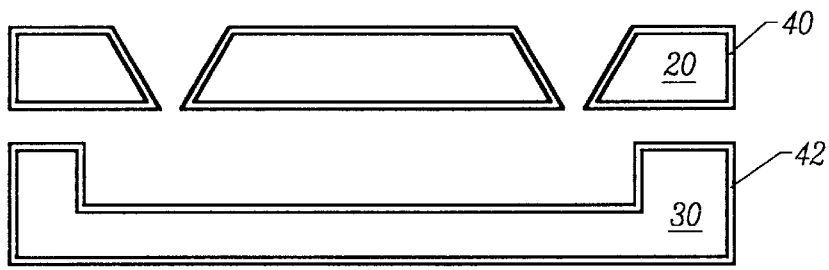
Figure 3D:
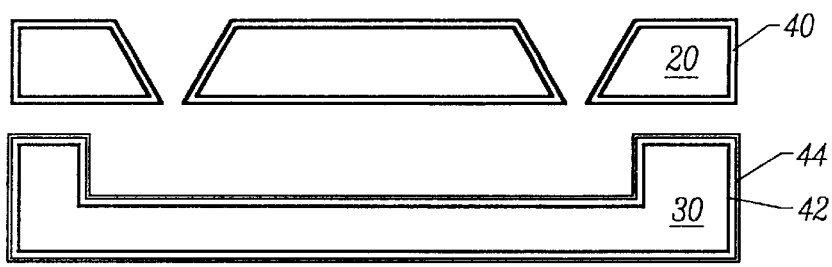
Figure 3E:
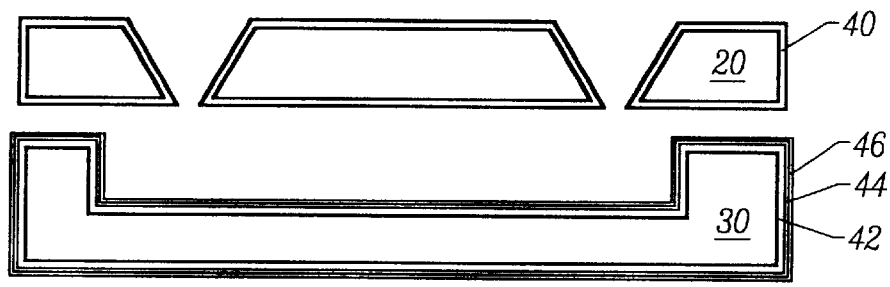

At this juncture, a top mold member 20 and a bottom mold member 30 are available. A perspective view of these elements is shown in FIG. 3a, and a side view of the same elements is shown in FIG. 3b. The following discussion is directed toward needle fabrication steps using these mold members. The top mold member 20 and the bottom mold member 30 are subjected to a standard wafer clean (Step A). Approximately 2 microns of phosphosilicateglass is then deposited on the top mold member 20 and the bottom mold member 30 FIG. 3c illustrates the resultant phosphosilicate glass (PSG) layer 40 on the top mold member 20 and the PSG layer 42 on the bottom mold member 30. The phosphoslicate glass is then reflowed (Step G). Approximately 0.5 microns of undoped polysilicon is then deposited (Step M) on the bottom mold member 30. The bottom mold member 30 is then subject to wet oxidation (Step V) to form an oxide of approximately 1 micron. The resultant silicon dioxide layer 44 is illustrated in FIG. 3d. Approximately 0.5 microns of undoped polysilicon is then deposited (Step M) on the bottom mold member 30 once again. The bottom mold member 30 is then subject to wet oxidation (Step V) to form an oxide of approximately 1 micron. The resultant silicon dioxide layer 46 is illustrated in FIG. 3e.

Figure 3F:
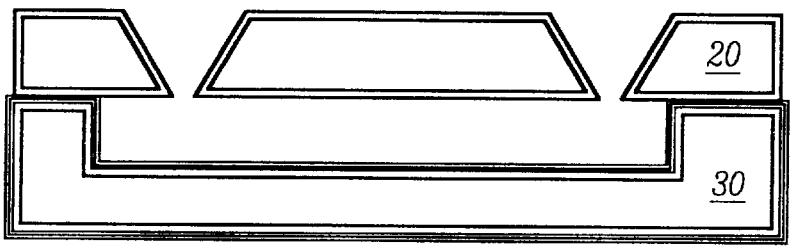

The top mold member 20 is then aligned with the bottom mold member 30. Standard techniques, including microscopic viewing techniques and alignment marks may be used in this step. The mold members are then pressure bonded together to produce the device of FIG. 3f.

Figure 3G:
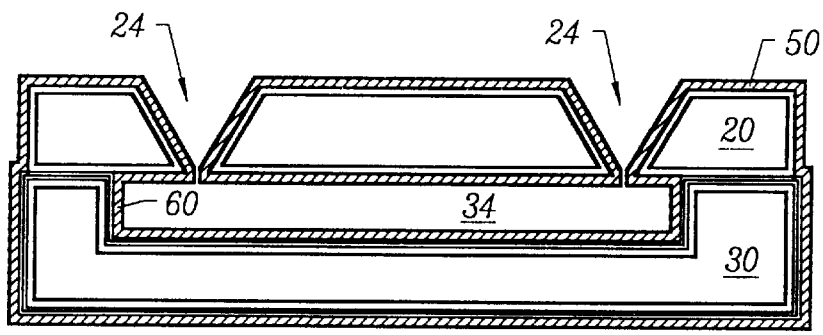
Figure 3H:
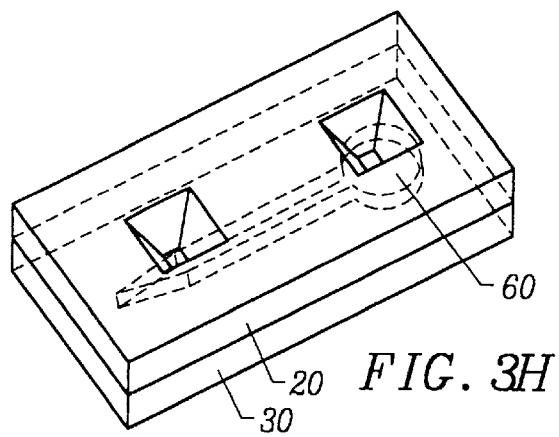

At this point, the needle can be formed by depositing a conformal substance into the mold. In particular, the conformal substance is passed through the deposition apertures into the enclosed, elongated needle trench. For example, approximately 0.3 microns of undoped polysilicon (Step M) may be deposited. Thereafter, a nitrogen anneal (Step O) is performed. The foregoing polysilicon and nitrogen anneal steps are repeated until the desired thickness of polysilicon is achieved. Six to fifteen microns of polysilicon is typical, depending on the strength and stiffness requirements. The resultant device is illustrated in FIG. 3g. In particular, the figure shows a polysilicon layer 50. The polysilicon layer 60 within the trench 34 defines a needle. FIG. 3h provides a perspective view of the device at this processing juncture.

An anisotropic polysilicon etch on the top side of the wafer sandwich of FIGS. 3g and 3h is then performed (Step N). The polysilicon thickness and a 75% over-etch are preferably performed. This operation results in the device of FIG. 3i. An anisotropic polysilicon etch on the bottom side of the wafer sandwich is then performed. The polysilicon thickness and a 25% over-etch are preferably performed, resulting in the device of FIG. 3j.

Figure 3I:
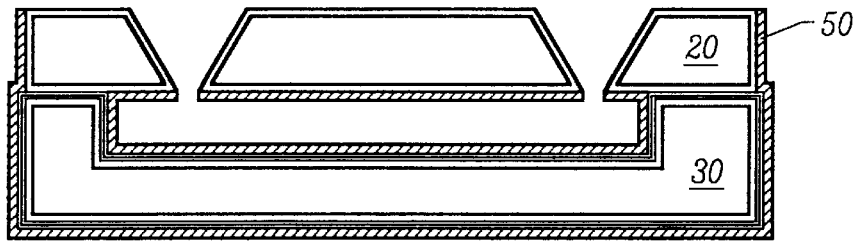
Figure 3J:
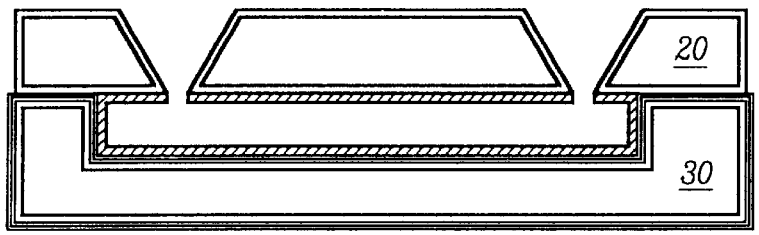
Figure 3K:
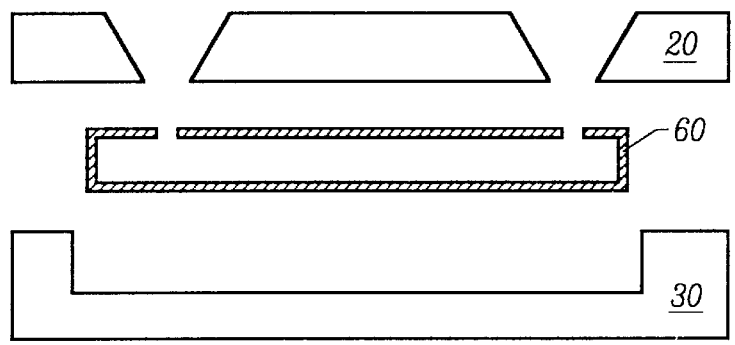
Figure 3L:
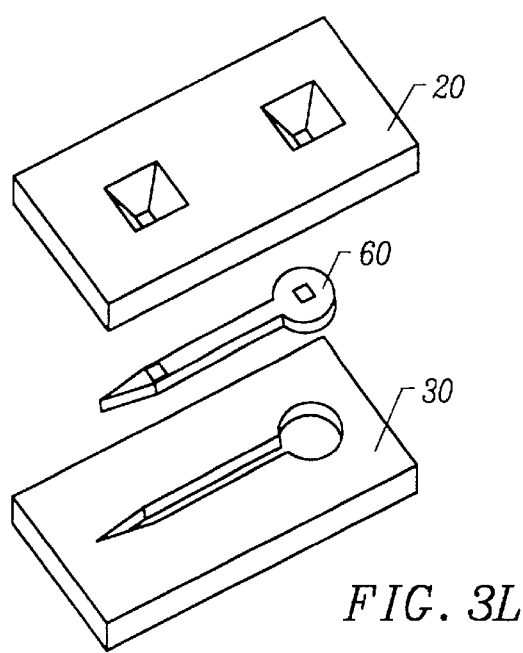

The sacrificial phosphosilicate glass layers 42 and 44 are then removed (Step S). The top mold member 20 and the bottom mold member 30 are then separated, and the resultant needle is released. FIG. 3k is a side view of the separated top mold member 20, bottom mold member 30, and released needle 60. FIG. 3i is a perspective view of the separated top mold member 20, bottom mold member 30, and released needle 60.

The released needle and mold members are then rinsed in DI water. The needle may be used at this point and the mold members may be re-used.

FIG. 4 is a perspective view of a needle 70 constructed in accordance with the disclosed processing steps. The needle 70 includes a fluid input port 72 and a set of fluid outlet ports 74. The operations described in relation to FIG. 1 are altered to produce additional deposition apertures in the top mold member so that the additional fluid outlet ports 74 may be provided. Observe that each deposition aperture in the top mold member results in a port in the resultant needle.

FIG. 5 is a perspective view of another needle 80 constructed in accordance with the processing steps of the invention. The needle 80 includes removal inhibiting barbs 82 and insertion limiting barbs 84. The operations described in relation to FIG. 2 are altered to provide a bottom mold member with the configuration corresponding to the barbs 82 and 84.

Figure 6:
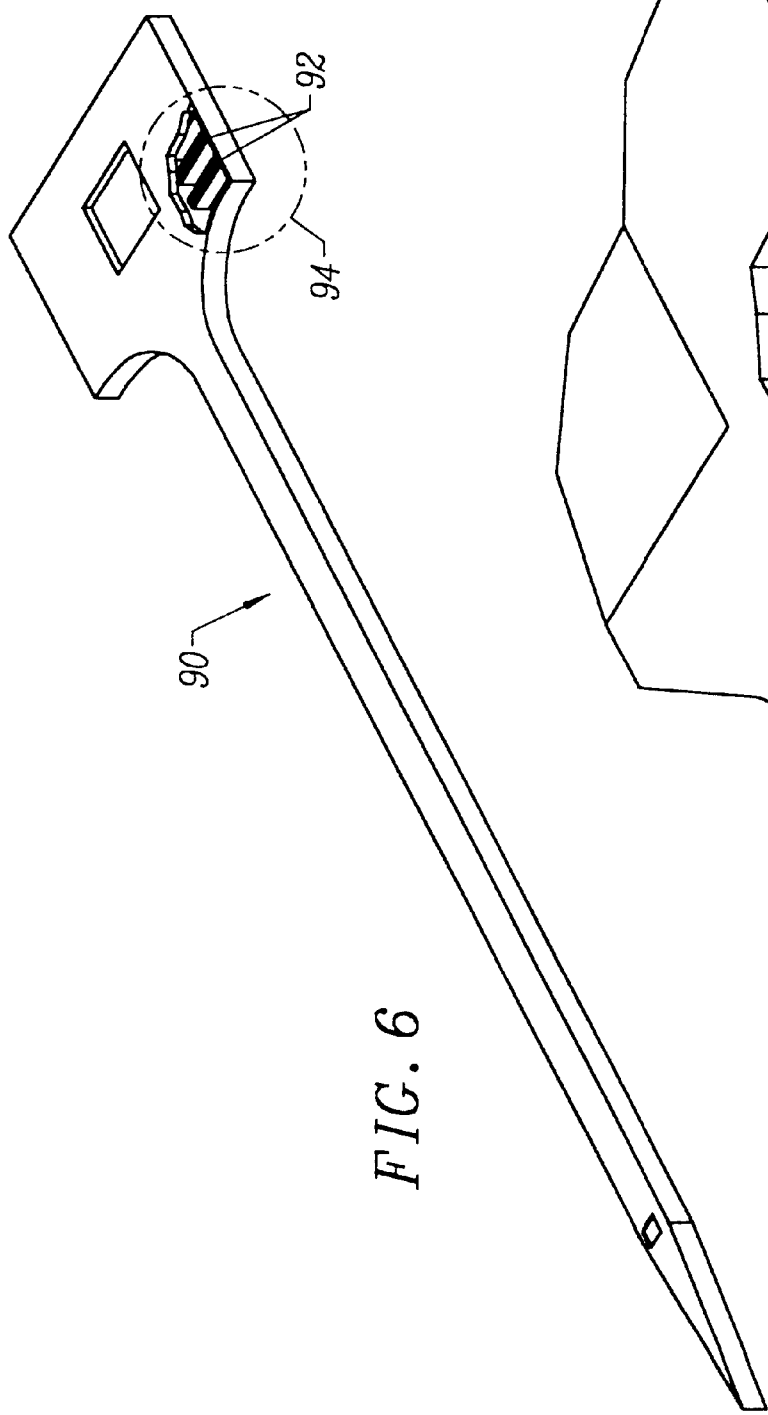
FIG. 6 is a perspective view of a needle with strength enhancement features in accordance with an embodiment of the invention.
Figure 7:
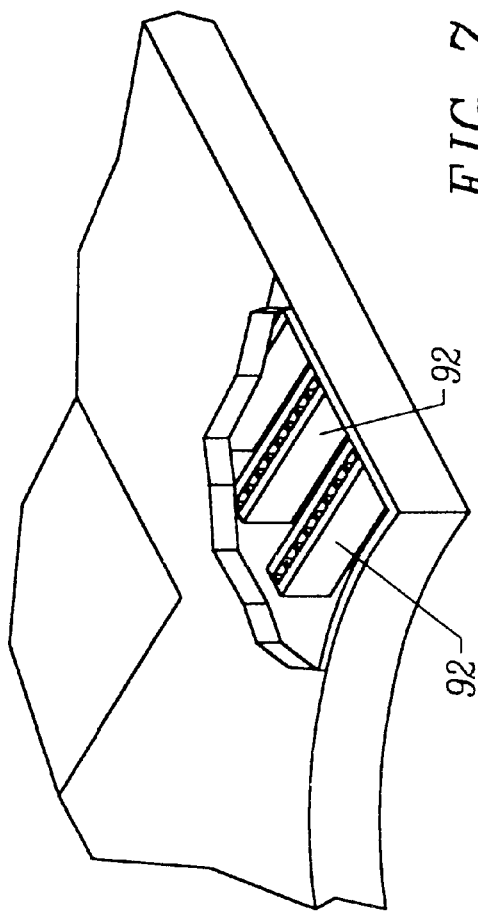
FIG. 7 is an enlarged view of the strength enhancement features of the needle of FIG. 6.

FIG. 6 is a perspective view of another needle 90 constructed in accordance with the processing steps of the invention. The needle 90 includes strength enhancement features. In accordance with the invention, strength enhancement features may be in the form of ribs, coatings, or bands. FIG. 6 illustrates internal ribs 92 for strength enhancement. FIG. 7 is an enlarged view of the region 94 of FIG. 6. FIG. 7 provides a more detailed view of the internal ribs 92. The operations described in relation to FIG. 2 are altered to provide the bottom mold member with ribs.

FIG. 8 is a perspective view of a dual prong needle 100 constructed in accordance with the processing steps of the invention. The needle 100 includes a first prong 102 and a second prong 104 joined at a hub 106. The operations described in relation to FIG. 2 are altered to provide the bottom mold member with the a trench to form the first prong 102 and a trench to form the second prong 104.

FIG. 9 is a perspective view of yet another needle 110 constructed in accordance with the processing steps of the invention. The needle 110 includes circuitry 112. The circuitry that may be incorporated into a needle of the invention includes electrodes, amplification circuitry, pumps, and biological sensors. Since the needle 110 is formed of poly silicon, standard processing techniques may be used to add the circuitry 112 to the needle 110.

Those skilled in the art will appreciate that various other geometries may be constructed in accordance with the disclosed processing steps. For example, multiple fluid cannulas, pumps, heaters, electrodes, and amplification circuitry may readily be incorporated into the needles of the invention. The simple needle shown in the figures can have any or all of these features added to it by easy modifications of the etch masks of the molds. To fabricate features or components of the needle such as heaters, electrodes, and amplification circuitry, the release etch must be timed such that the molds are separated, but the needles are still embedded in the mold cavities of the bottom mold wafer. This partial release process step may be aided by using only silicon dioxide as the release layer around the needle, but still using PSG for the wafer to wafer bonding. This change will aid partial release because PSG is etched much faster than silicon dioxide. After this step, further processing can be done to the bottom mold wafer alone to put the features or components mentioned above on the needles. Heaters and/or electrodes can be fabricated by a metal or doped polysilicon deposition and subsequent masking and etching. Amplification circuitry can be added using a CMOS, NMOS, bipolar or FET process. All features that are made of materials other than silicon may be damaged by the concentrated HF release etch, so they should be protected by a layer of polysilicon or other material that is resistant to HF.

Needles of the invention have been fabricated on a 100 mm wafer. In particular, over a 1000 needles with lengths of 3 and 6 mm have been fabricated with a 100 mm wafer. Needles up to two inches long may be fabricated in accordance with the invention. For such an embodiment, the deposition apertures in the top mold member 20 must be enlarged.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

We claim:

1. A method of fabricating a needle via conformal deposition in a two-piece mold, said method comprising the steps of:

attaching a top mold member to a bottom mold member such that said top mold member and said bottom mold member define an enclosed, elongate needle trench with a deposition aperture;

passing a conformal substance through said deposition aperture such that said conformal substance is deposited via vapor deposition within said enclosed, elongated needle trench;

stopping said passing step before said elongated needle trench is filled with said conformal substance; and removing said top mold member and said bottom mold member to expose a needle.

2. The method of claim 1 wherein said passing step includes the step of passing polysilicon through said deposition aperture.

3. The method of claim 2 wherein said passing step is repeated until said polysilicon is deposited to a desired depth.

4. The method of claim 1 wherein said passing step includes the step of passing said conformal substance through said deposition aperture such that said conformal substance is deposited within said enclosed, elongated needle trench, which defines a dual prong needle.

5. The method of claim 1 wherein said passing step includes the step of passing said conformal substance through said deposition aperture such that said conformal substance is deposited within said enclosed, elongated needle trench, which defines a barb.

6. The method of claim 1 wherein said passing step includes the step of passing said conformal substance through said deposition aperture such that said conformal substance is deposited within said enclosed, elongated needle trench, which defines a strength enhancement feature.

* * * * *